United States Patent [19]
Bare et al.

[11] Patent Number: 5,652,239
[45] Date of Patent: Jul. 29, 1997

[54] PYRIDAZINEDIONE DERIVATIVES USEFUL IN TREATMENT OF NEUROLOGICAL DISORDERS

[75] Inventors: Thomas Michael Bare, West Chester, Pa.; James Franklin Resch, Bear, Del.; Paul Francis Jackson, Chadds Ford, Pa.

[73] Assignee: Imperial Chemical Company, London, England

[21] Appl. No.: 545,229

[22] Filed: Oct. 19, 1995

Related U.S. Application Data

[63] Continuation of Ser. No. 880,962, May 8, 1992, abandoned.

[30] Foreign Application Priority Data

May 9, 1991 [GB] United Kingdom ............... 9109972

[51] Int. Cl.⁶ .................... A61K 31/50; C07D 487/04; C07D 495/14; C07D 471/14
[52] U.S. Cl. .................... 514/248; 544/234; 544/236; 548/492; 560/43; 564/311
[58] Field of Search ............... 544/234; 514/248

[56] References Cited

FOREIGN PATENT DOCUMENTS

3121137A1 12/1982 Germany .
494647A1 8/1981 Spain .

OTHER PUBLICATIONS

Monge et al J. Med. Chem., 34, 3023–3029 (1991).
Monge et al Acta Farm. Bonaerense, 3(1), 21–6 (1984).
Monge–Vega et al. J. Pharm. Sci, 71(12), 1406–8, (1982).
Monge–Vega et al. J. Heterocyclic Chem., 18, 1533 (1981).
Kurasawa et al., "A Convenient Synthesis of Pyridazino[4,5-b]quinolines and Pyrrolo[3,4-b]quinolines" *Chem. Pharm. Bull.*, (1980) 28, No. 12, 3457–3465.
Ferguson et al., "Selected Pharmacological Studies of a Series of Substitued Imidazo(4,5-d)pyridazines" *J. Pharm. Sci.*, (1970) 59, No. 11, 1584–1586.

*Primary Examiner*—Emily Bernhardt
*Attorney, Agent, or Firm*—Michael D. Alexander

[57] ABSTRACT

The present invention relates to pyridazino[4,5-b]indoles, and pharmaceutically useful salts thereof, which are excitatory amino acid antagonists and which are useful when such antagonism is desired such as in the treatment of neurological disorders. The invention further provides pharmaceutical compositions containing pyridazino[4,5-b]indoles as active ingredient, and methods for the treatment of neurological disorders.

7 Claims, No Drawings

PYRIDAZINEDIONE DERIVATIVES USEFUL IN TREATMENT OF NEUROLOGICAL DISORDERS

This application is a continuation of our prior application Ser. No. 07/880,962, filed May 8, 1992 now abandoned.

This invention relates to pyridazinedione compounds useful in the treatment of neurological disorders generally in mammals such as man. More specifically, the compounds are useful in the treatment of strokes and/or other neurodegenerative disorders such as hypoglycemia, cerebral palsy, transient cerebral ischemic attack, perinatal asphyxia, epilepsy, psychosis, Huntington's chorea, amyotrophic lateral sclerosis, Alzheimer's disease, Parkinson's disease, Olivo-pontocerebellar atrophy, viral-induced neurodegeneration such as in acquired immunodeficiency syndrome and its associated dementia, anoxia such as from drowning, spinal cord and brain trauma, and chronic pain, for the prevention of drug and alcohol withdrawal symptoms, and for the inhibition of tolerance and dependence to opiate analgesics. The invention particularly relates to novel pyridazinedione compounds useful in reducing neurological degeneration such as can be induced by a stroke and the associated functional impairment which can result. Treatment using a compound of the invention can be remedial or therapeutic as by administering a compound following an ischemic event to mitigate the effects of that event. Treatment can also be prophylactic or prospective by administering a compound in anticipation that an ischemic event may occur, for example in a patient who is prone to stroke.

It is known that ischemic events can trigger a dramatic increase in extracellular concentrations of the excitatory amino acids glutamate and aspartate which can, in turn, cause prolonged neuronal excitation leading to a massive influx of calcium from extracellular to intracellular sites in brain neural cells. A calcium overload can thereby be created which leads to a cascade of events leading to cell catabolism and eventually resulting in cell death. The N-methyl-D-aspartate (NMDA) receptor complex is believed to play a significant role in the cascade of events leading to cell necrosis following an ischemic event.

The compounds provided by this invention may be useful in a variety of neurodegenerative disorders because they function as excitatory amino acid antagonists. They may do so indirectly, via allosteric modulation of the glutamate binding site, specifically by acting as antagonists of the strychnine-insensitive glycine receptor on the NMDA receptor complex. They may also do so directly, by binding to the glutamate site itself on the NMDA receptor complex.

According to the invention there is provided a compound of formula I (formula set out, together with other formulae referred to by Roman Numerals, on pages following the Examples), or a pharmaceutically acceptable salt thereof, wherein Ring A is selected from the members shown as formulae Ia–Ih, wherein $R^4$, $R^5$, $R^6$, and $R^7$ are independently selected from the group consisting of hydrogen, halo, (1–4C)alkyl which may contain a double or triple bond, (1–3C)perfluoroalkyl, (1–3C)alkyl substituted with trifluoromethyl, nitro, hydroxy, methoxy, ethoxy, $CO_2R_2^b$, $CONHR^b$, $CONR_2^b$, CN, and cyclopropyl, wherein $R^b$ is selected from hydrogen and (1–4C)alkyl; but excluding compounds wherein, when ring A has formula Ia, $R^4$–$R^7$ are each hydrogen.

The invention further provides a method for the treatment of neurological disorders, comprising administering to a mammal in need of such treatment an effective amount of a compound of formula I as defined above, or a pharmaceutically acceptable salt thereof.

The invention further provide a pharmaceutical composition for the treatment of neurological disorders comprising a compound of formula I as defined above, and a pharmaceutically acceptable diluent or carrier.

It will be appreciated that within the above definitions there are included a number of subgroups of compounds, for example:

(a) compounds of formula IIa;
(b) compounds of formula IIb;
(c) compounds of formula IIc;
(d) compounds of formula IId;
(e) compounds of formula IIe;
(f) compounds of formula IIf;
(g) compounds of formula IIg; and
(h) compounds of formula IIh.

In the formulae (IIa)–(IIh), $R^4$–$R^7$ are as previously defined. The above subgroups of compounds include salts thereof, especially the pharmaceutically acceptable addition salts.

It will be appreciated by those skilled in the art that certain compounds of formula I contain an asymmetrically substituted carbon atom, and accordingly may exist in, and be isolated optically-active and racemic forms. In addition, it will be appreciated that certain compounds of formula I, for example, those containing a double bond, may exist in, and be isolated in, separate stereoisomeric forms ('E' and 'Z') about that group. Some compounds may exhibit polymorphism. It is to be understood that the present invention encompasses any racemic, optically-active, polymorphic or stereoisomeric form, or mixtures thereof, which form possesses properties useful in the treatment of neurodegenerative disorders, it being well known in the art how to prepare optically-active forms (for example, by resolution of the racemic form or by synthesis from optically-active starting materials) and individual 'E' and 'Z' stereoisomers (for example, by fractional crystallization or chromatographic separation of a mixture thereof) and how to determine neuroprotective properties by the standard tests described hereinafter.

It will be further appreciated by those skilled in the art that compounds of formula I can exist and be drawn in various tautomeric forms such as the generic formulae shown as formulae IIIa–IIIc. It is to be understood that all references to any particular structure are understood to include the various tautomeric forms thereof.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

Particular values of (1–4C)alkyl include methyl, ethyl, propyl, isopropyl, butyl, isobutyl, sec-butyl, and tert-butyl.

Particular values of (1–4C)alkyl containing a double or triple bond include ethenyl, prop-1-enyl, prop-2-enyl (i.e. allyl), ethynyl, prop-1-ynyl, prop-2-ynyl (i.e. propargyl), and but-2-enyl.

Particular values of halo include fluoro, chloro, bromo, and iodo.

Particular values of (1–3C)perfluoroalkyl include trifluoromethyl, pentafluoroethyl, and heptafluoropropyl.

Particular values of (1–3C)alkyl substituted with a trifluoromethyl group include trifluoromethylmethyl, 2-trifluoromethylethyl, 1-trifluoromethylethyl, and 1-trifluoromethylpropyl.

More particular values of (1–4C)alkyl include methyl, ethyl, propyl, and isopropyl.

More particular values of (1–4C)alkyl which can contain a double or triple bond include methyl, ethyl, propyl, ethenyl, prop-1-enyl, prop-2-enyl, ethynyl, and prop-2-ynyl.

More particular values of (1–3C)perfluoroalkyl include trifluoromethyl and pentafluoroethyl.

More particular values of (1–3C)alkyl substituted with a trifluoromethyl group include trifluoromethylmethyl, 2-trifluoromethylethyl and 1-trifluoromethylethyl.

More particular values of halo include chloro, bromo, and iodo.

Preferred values of $R^4$–$R^7$ include hydrogen, fluoro, chloro, bromo, iodo, methyl, ethyl, propyl, allyl, propargyl, trifluoromethyl, pentafluoroethyl, trifluoromethylmethyl, nitro, methoxy, ethoxy, propoxy, and cyano.

More preferred values of $R^4$–$R^7$ include hydrogen, fluoro, chloro, bromo, iodo, methyl, ethyl, trifluoromethyl, nitro, methoxy, and cyano.

Preferred compounds having formula I include:
7,9-dichloro-8-methoxypyridazino[4,5-b]indole-1,4-dione;
7,9-dichloropyridazino[4,5-b]indole-1,4-dione;
7-trifluoromethylpyridazino[4,5-b]indole-1,4-dione;
7-bromopyridazino[4,5-b]indole-1,4-dione;
7-chloropyridazino[4,5-b]indole-1,4-dione;
7-iodopyridazino[4,5-b]indole-1,4-dione;
7,9-dibromopyridazino[4,5-b]indole-1,4-dione;
7-methoxypyridazino[4,5-b]indole-1,4-dione;
6-methoxypyridazino[4,5-b]indole-1,4-dione; and
7,9-ditrifluoromethylpyridazino[4,5-b]indole-1,4-dione;

Pyridazinediones of formula I can be made by processes which include processes known in the chemical arts for the production of structurally analogous compounds. Such processes for the manufacture of a pyridazinedione of formula I as defined above are provided as further features of the invention and are illustrated by the following procedures in which the meanings of generic radicals are as given above unless otherwise qualified. Such a process can be effected, generally, by treating a diester of formula IV, wherein $R^{13}$ is (C1–C3)alkyl, with hydrazine. It is noted that higher alkyl diesters can be employed, but that no advantage is gained.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

Certain diesters of formula IV for use in a process as described herein can be made by heating a corresponding compound of formula V at a temperature of 150°–220° C. and in a suitable solvent such as o-xylene or diphenyl ether to effect ring closure and thereby yield the desired diester. The compound of formula V is preferably, for ease of workup, isolated, e.g. by flash column chromatography on silica gel to make the corresponding compound of formula IV. However, the compound of formula V need not be purified and can be carried into the next step without purification.

A compound of formula V can be made by treating a corresponding substituted hydrazobenzene of formula VI with a dialkyl acetylenedicarboxylate, such as diethyl acetylenedicarboxylate, in a suitable solvent such as a (C1–C4)alcohol. As solvent, ethanol is preferred.

A compound of formula VI can be made by reducing a corresponding nitro compound of formula VII with zinc, preferably in the presence of aqueous base (such as an aqueous alkali metal hydroxide, e.g. sodium, potassium, or lithium hydroxide).

It is noted that many of the starting materials for synthetic methods as described above are commercially available and/or widely reported in the scientific literature, for example nitro compounds of formula VII.

Examples of suitable pharmaceutically acceptable salts are salts formed with bases which form a physiologically acceptable cation, such as alkali metal (especially lithium, sodium and potassium), alkaline earth metal (especially calcium and magnesium), aluminum and ammonium salts, as well as salts made with appropriate organic bases such as choline hydroxide, triethylamine, morpholine, piperidine, ethylenediamine, lysine, ethanolamine, diethanolamine, triethanolaminem, N-methyl-D-glucamine (meglumine), arginine, and tris(hydroxymethyl) aminomethane.

When used to intervene therapeutically following a stroke, a pyridazinedione of formula I generally is administered as an appropriate pharmaceutical composition which comprises a pyridazinedione of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous or intramuscular injection or infusion; and in the form of powders together with pharmaceutically acceptable inert solid diluents such as lactose for administration by insufflation.

The dose of compound of formula I which is administered will necessarily be varied according to principles well known in the art taking account of the route of administration, the severity of the postischemic disorder, and the size and age of the patient. In general, a compound of formula I will be administered to a warm blooded animal (such as man) so that an effective dose is received, generally a dose in the range of about 0.01 to about 100 mg/kg body weight. For example, if the compound is administered intravenously, it is administered in the range of about 0.01 to about 20 mg/kg body weight. If it is administered orally, it is administered in the range of about 0.5 to about 100 mg/kg body weight.

It will be apparent to those skilled in the art that a compound of formula I can be co-administered with other therapeutic or prophylactic agents and/or medicaments that are not medically incompatible therewith. Compounds within the scope of the invention do not show any indication of untoward side-effects in laboratory test animals at several multiples of the minimum effective dose.

The actions of compounds of formula I as antagonists at the glycine receptor of the NMDA receptor complex can be shown by one or more standard tests such as the [$^3$H]-glycine binding assay (Test A), by functional assays in vitro such as tests for measuring glutamate-evoked contractions of the guinea pig ileum (Test B) and/or tests for measuring antagonism of NMDA-induced evoked response in hippocampal slices (Test C), and by tests in vivo such as ischemia induced by carotid occlusion in the gerbil model (Test D).

Test A

In the [$^3$H]-glycine binding assay, neuronal synaptic membranes are prepared from adult (about 250 g) male Sprague-Dawley rats. Freshly dissected cortices and hippocampi are homogenized in 0.32M sucrose (110 mg/mL). Synaptosomes are isolated by centrifugation (1000 xg, 10 min), the supernatant is pelleted (20,000 xg, 20 min) and resuspended in double-distilled water. The suspension was centrifuged for 20 minutes at 8,000 xg. The resulting supernatant and buffy coat are washed twice (48,000 xg, 10 mins, resuspension in double-deionized water). The final pellet is quickly frozen (dry ice/ethanol bath) under double-deionized water and stored at −70° C.

On the day of the experiment, thawed synaptic membranes are homogenized with a Brinkmann Polytron (™, Brinkmann Instruments, Westbury, N.Y.) tissue homogenizer in 50 millimolar tris(hydroxymethyl)aminomethane citrate, pH 7.1. The membranes are incubated with 0.04% Sufact-AMPS X100 (™, Pierce, Rockford, Ill.) in buffer for 20 minutes at 37° C. and washed six times by centrifugation (48,000 xg, 10 min) and resuspended in buffer. The final pellet is homogenized at 200 mg wet weight/mL of the buffer for the binding assay.

For [$^3$H]-glycine binding at the N-methyl-D-aspartate receptor, 20 nanomolar [$^3$H]-glycine (40–60 Ci/mmol, New England Nuclear, Boston, Mass.) is incubated with the membranes suspended in 50 millimolar tris (hydroxymethyl)aminomethane citrate, pH 7.1 for 30 minutes at 4° C. Glycine, 1 millimolar, is used to define the nonspecific binding. Bound [$^3$H]-glycine is isolated from free using a Brandel (Biomedical Research and Development Laboratories, Gaithersburg, Md.) cell harvester for vacuum filtration over glass fiber filters (Whatman GF/B from Brandel, Gaithersburg, Md.) presoaked in 0.025% polyethylenimine. The samples retained on the glass fiber filters are rinsed 3 times with a total of 2.5 mL ice cold buffer. Radioactivity is estimated by liquid scintillation counting. $IC_{50}$ values are obtained from a least-squares regression of a logit-log transformation of the data. Typical $IC_{50}$ values for compounds of the invention are usually less than 100 μM (micromolar) and are illustrated by the compound of Example 1 ($IC_{50}$=0.55 μM), Example 4 ($IC_{50}$=0.33 μM), and Example 7 ($IC_{50}$=2.7 μM).

Test B

For glutamate-evoked contractions of the guinea pig ileum, the methodology is as described previously (Luzzi et. al., Br. J. Pharmacol., 95, 1271–1277 (1989)). The longitudinal muscle and associated myenteric plexus are removed and placed in oxygenated modified Krebs-Henseleit solution (118 millimolar NaCl, 4.7 millimolar KCl, 2.5 millimolar CaCl$_2$, 1.2 millimolar KH$_2$PO$_4$, 25 millimolar NaHCO$_3$, and 11 millimolar glucose). Tissues are suspended on glass rods in organ baths under a resting tension of 0.5 g. After an initial depolarization with 80 millimolar potassium ion to remove possible blockade of the NMDA receptor channel complex with magnesium ion, twitch responses are evoked with 100 micromolar glutamate. Isometric mechanical responses are recorded. Tissues are equilibrated for at least 2 hours prior to addition of compounds.

A dose response curve for the effect of the unknown on the magnitude of the glutamate-evoked contractions is generated. Glutamate-evoked contractions are generated at 20 minute intervals, with the test compound added 5 minutes before the glutamate. The magnitude of the contraction with each dose of the unknown is expressed relative to the control, the third contraction evoked by 100 micromolar glutamate alone in the same tissue bath. The $IC_{50}$ is obtained from a least-squares regression of a logit-log transformation of the data.

After the last contraction for the dose-response curve, 100 micromolar glycine is added to the bath 10 minutes after the previous addition of glutamate. Ten minutes later the estimated $IC_{50}$ to $IC_{70}$ dose of the test compound is added and 10 minutes later glutamate is used to evoke the contraction. The "glycine reversal" is the ability of glycine to compete with the unknown and to prevent the inhibition previously seen by the dose of the unknown. Typical $IC_{50}$ values are usually less than 1000 μM and are illustrated by the compound of Example 1 ($IC_{50}$=13 μM), Example 4 ($IC_{50}$=6.4 μM), and Example 7 ($IC_{50}$=69 μM).

Test C

The characterization of a compound as a glycine antagonist in the hippocampal slice test (HST) is dependent on (1) the ability of the compound to inhibit NMDA receptor-mediated synaptic transmission in hippocampal slices and (2) the subsequent reversal of these inhibitory effects by D-serine. All the experiments are carried out under conditions of low magnesium ion (Mg++) in order to unmask the NMDA receptor, which at normal Mg++ levels is blocked and therefore does not participate in synaptic transmission.

The procedure for the HST is as follows. Transverse hippocampal slices are obtained from male Sprague-Dawley rats weighting 80–150 gm. The rats are decapitated and the brains quickly removed and placed in cold Krebs-Ringer solution which contains (in millimolar) NaCl (122.6), NaHCO$_3$ (26.2), KCl (5.4), MgSO$_4$ (2.0), NaH$_2$PO$_4$ (1.2), CaCl$_2$ (2.0), and D-glucose (10.0). The hippocampus is dissected free from surrounding tissues, and 495 microns thick slices are cut and immediately transferred to a humidified static interface chamber with a 95% O$_2$:5% CO$_2$ atmosphere at room temperature. Following a 1-hour equilibration period, slices are placed one at a time into a small perfusion chamber where they are completely submerged in continuously flowing oxygenated 2 millimolar Mg++ perfusate (4 mL/min) at 33° C. and allowed to equilibrate for 10 to 15 min.

For the electrophysiology part of the experiments, bipolar tungsten stimulating electrodes are positioned in the stratum radiatum of the CA3 cell body region of the hippocampus and a single-barrel glass microelectrode filled with Krebs-Ringer solution is positioned in the CA1 cell body region. Low frequency stimulation is then applied to area CA3 which evokes a primary population spike (PS) recorded from CA1. The primary PS represents the summation of a multiple of synaptic potentials mediated via the quisqualate receptor. The stimulus intensity is adjusted to evoke a PS of 1–4 mV amplitude and is maintained at this intensity throughout the experiment.

When the perfusion medium is then changed from 1 millimolar Mg++ to one containing 0 Mg++, the primary PS is followed by the appearance of many secondary PSs. The appearance of the secondary PSs are attributed to the unmasking of NMDA-mediated synaptic events in 0 Mg++. By bathing hippocampal slices in 0 Mg++, drug effects can be qualitatively assessed by measuring the ability of a compound to inhibit the secondary PSs. The effects of directly acting NMDA and indirectly acting NMDA (ie, glycine) receptor antagonists can also be differentiated by the ability of D-serine to reverse this inhibition. Thus, glycine antagonists, such as 7-chlorokynurenic acid and HA-966, will inhibit the secondary PSs and this inhibition is reversed by D-serine, a glycine agonist. In contrast, the inhibition produced by selective competitive NMDA receptor antagonists, such as CPP and APV, or non-competive NMDA receptor antagonists, such as PCP and MK-801, is not reversed by D-serine.

For a particular test compound the HST typically is evaluated at a multiple, for example a multiple of 5, of the IC$_{50}$ concentration obtained in Test B, it being ascertained that the test compound exhibits glycine antagonism at the concentration employed. The HST is accordingly confirmatory of Test B. Typical concentration results are illustrated by the compound of Example 1 (15.2 μM, antagonist, reversible by D-serine) and Example 4 (10 μM, antagonist, reversible by D-serine).

Test D

When testing in vivo using the gerbil ischemic model, adult female Mongolian gerbils (50–70 g) are anesthetized with 2 to 3% halothane. The bilateral common carotid arteries at the neck are exposed and occluded with microaneurysm clips. After 10 min (unless specified), the clips are removed and the blood flow through the carotid arteries is restored and the skin is sutured. Test compounds are administered intraperitoneally both pre- and post-occlusion, for example 45 minutes before and 5 minutes after occlusion of the carotid arteries. Sham-operated animals are treated in the same manner except that the arteries are not clamped. Gross behavioral observations along with motor activity are recorded for 2 hr on the first (24 hr) day following the occlusion. After 4 days, subjects are sacrificed (decapitation), brains are removed, fixed, sectioned and stained with hematoxylin/eosin and cresyl violet.

The brain sections are rated for neuronal damage in the hippocampus using the following rating scale:

0=undamaged, normal

1=slight damage (up to 25%)—restricted to CA1/subiculum border

2=moderate damage (up to 50%)—obvious damage, restricted to less than half of CA1 field 3=marked damage (up to 75%)—involving greater than half of CA1 field 4=damage extending beyond CA1 field Sections (7 micron) are evaluated from each brain. Occasionally, asymmetrical damage may be noted and the rating assigned is the average score of the two sides. The average brain damage rating score for each group is recorded, and the damage scores of the drug treated group are compared to the vehicle-treated group using Wilcoxon-Rank Sum test.

Typical values in this test for compounds according to the invention are illustrated by the following results: 34% neuroprotection (relative to sham-operated control) for the compound of Example 1, and over 75% neuroprotection for the compound of Example 4, when each compound was administered intraperitoneally (ip) at a level of 10 mg/Kg body weight according to the above regimen.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) evaporation of solvent was carried out using a rotary evaporator under reduced pressure (600–4000 Pascals; 4.5–30 mm Hg) with a bath temperature of up to 60° C.;

(iii) flash chromatography was carried out on Merck Kieselgel (Art 9385) and column chromatography on Merck Kieselgel 60 (Art 7734); [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) reduced pressures are given as absolute pressures in Pascals (Pa); other pressures are given as gauge pressures in bars;

(ix) chemical symbols have their usual meanings; the following abbreviations have also been used: v (volume), w (weight); mp (melting point), L [liter(s)], mL (milliliters), mM (millimoles), g [gram(s)], mg [milligram(s)], min (minutes), h (hour); and (x) solvent ratios are given in volume: volume (v/v) terms.

EXAMPLE 1

7-Chloropyridazino[4,5-b]indole-1,4-dione

To a stirred solution of diethyl 6-chloro-2,3-dicarboxylate (0.75 g, 2.5 mM) was added hydrazine hydrate (4.13 g, 80 mM). The solution was heated to reflux for 2 hours during which time a precipitate formed. The reaction mixture was then cooled to room temperature, the precipitate filtered, and washed with ethanol. The solid was then added to glacial acetic acid (4.5 mL), warmed to reflux, cooled, filtered and dried. This afforded the titled compound as a white solid (0.42 g, 70%), mp >250° C.

Analysis for $C_{10}H_6N_3O_2Cl$: Calculated: C, 50.97; H, 2.57; N, 17.83; Found: C, 50.58; H, 2.72; N, 17.73.

The starting diethyl 6-chloroindole-2,3-dicarboxylate was prepared as follows:

a. 3,3'-Dichlorohydrazobenzene

To a stirred solution of 50% NaOH (3 mL) was added 3-chloronitrobenzene (10 g, 64 mM). The suspension was warmed to 60° C. and zinc (9 g, 138 mM) was added. During the addition, the temperature of the reaction mixture was kept between 60° and 80° C. After the addition was complete, a solution of 20% NaOH (18 mL, 90 mM) was added followed by water (30 mL). An additional portion of zinc (12 g, 189 mM) was then added and the resulting mixture was stirred between 75°–80° C. for 2 hours. After cooling to room temperature, the mixture was added to ether (200 mL), stirred, and the liquid was decanted. The solids were then resuspended in ether and the extraction was repeated 3 times. The ether extracts were combined, dried (Na$_2$SO$_4$), and concentrated to give a yellow solid. This was purified by flash column chromatography using CH$_2$Cl$_2$ as elutant which afforded the titled compound as a yellow solid (5.5 g, 68%). NMR (CDCl$_3$): 7.12 (t, J=8 Hz, 2H), 6.80 (m, 4H), 6.67 (dd, J$_1$=1 Hz, J$_2$=8 Hz, 2H), 5.66 (br s, 2H).

b. Diethyl 4-Chloroindole-2,3-dicarboxylate and Diethyl 6-Chloro-indole-2,3-dicarboxylate Diethyl acetylenedicarboxylate (3.72 g, 21.8 mM) was added to a stirred solution of 3,3'-dichlorohydrazobenzene (5.5 g, 21.8 mM) in 75 mL of methanol. The resulting solution was then heated to reflux for 17 hours. The reaction was cooled to room temperature and concentrated. The resulting oil was purified by flash column chromatography to provide 5.1 g of a yellow solid. This was added to diphenyl ether (5 mL) and heated to 200° C. for 2 hrs. The solution was then cooled to room temperature and applied directly to a silica gel column. Elution with methylene chloride provided 1.7 g of a mixture of diethyl 4-chloroindole-2,3-dicarboxylate and diethyl 6-chloroindole-2,3-dicarboxylate. Separation of the isomers was effected by further flash column chromatography and afforded diethyl 6-chloroindole-2,3-dicarboxylate (0.75 g, 11%) as a white solid and diethyl 4-chloroindole-2,3-dicarboxylate (0.70 g, 11%) as a yellow solid. Spectra: Diethyl 6-chloroindole-2,3-dicarboxylate: NMR ($d_6$-DMSO): 7.92 (d, 1H), 7.53 (s, 1H), 7.25 (d, 1H), 4.34 (m, 4H), 1.33 (m, 6H). MS(CI): 296(M+1). Diethyl 4-chloroindole-2,3-dicarboxylate: NMR ($d_6$-DMSO): 7.47 (d, J=8 Hz, 1H), 7.32 (t, J=7 Hz, 1H), 7.22 (d, J=7 Hz, 1H), 4.33 (m, 4H), 1.31 (m, 6H). MS(CI): 296(M+1).

EXAMPLE 2

8-Chloropyridazino[4,5-b]indole-1,4-dione

To a stirred solution of diethyl 5-chloroindole-2,3-dicarboxylate (0.21 g, 0.71 mM) in ethanol (1 mL) was added hydrazine hydrate (1 ml, 20 mM). The mixture was warmed to reflux for two hours, cooled to room temperature, and the resulting solid was filtered. This was then suspended in acetic acid (1.5 mL) and warmed briefly to reflux. After cooling to room temperature, the solid was filtered, washed with water, and then with hot methanol. This afforded the titled pyridazinedione (60 mg, 36%) as a white solid, mp >250° C. NMR ($d_6$-DMSO, 250 MHz): 12.73 (s, 1H), 11.65 (s, 2H), 8.04 (d, J=2 Hz, 1H), 7.61 (d, J=9 Hz, 1 H), 7.46 (dd, $J_1$=2 Hz, $J_2$=9 Hz). MS(M+1): 236.

Analysis for $C_{10}H_6N_3O_2Cl$: Calculated: C, 50.97; H, 2.57; N, 17.83; Found: C, 50.91; H, 2.77; N, 17.61.

The starting diethyl 5-chloroindole-2,3-dicarboxylate was prepared as follows:

a. 4,4'-Dichlorohydrazobenzene

A suspension of 4-chloronitrobenzene (2.5 g, 15.9 mM) in 50% aqueous NaOH (1 mL, 12.5 mM) was warmed to 60° C. Zinc dust (3 g, 46 mM) was added in portions at such a rate as to keep the reaction temperature below 80° C. After all the zinc had been added, the reaction mixture was diluted with 20% NaOH (6 mL, 30 mM) and water (10 mL). A second portion of zinc dust (4 g, 62 mM) was then added in one portion. The resulting reaction mixture was stirred at 80° C. for approximately 18 hrs. The mixture was cooled to room temperature, the solid was filtered, and washed several times with ether. The combined filtrates were concentrated and purified by flash column chromatography. This afforded the title compound as a yellow solid (1.25 g, 5 mM) which contained approximately 25% of an impurity. This mixture was used directly in the next step. NMR ($d_6$-DMSO, 250 MHz): 7.14 (d, J=9 Hz, 4H), 6.76 (d, J=9 Hz, 4H), 5.63 (br s, 2H).

b. Diethyl 5-Chloroindole-2,3-dicarboxylate

To a stirred solution of 4,4'-dichlorohydrazobenzene (1.2 g, 4.7 mM) in methanol (20 mL) was added diethyl acetylenedicarboxylate (1 mL, 6.0 mM). The resulting solution was heated to reflux for 17 hrs. At the end of this time, the reaction mixture was cooled to room temperature during which time a precipitate formed. This was filtered and then dissolved in diphenyl ether (2 mL). The resulting solution was heated to 200° C. for two hours. The reaction mixture was then cooled, diluted with hexane, and the resulting solid filtered and dried. This afforded the titled compound as a yellow solid (0.21 g, 40%) which was used without further purification in the next step. NMR (CDCl$_3$, 300 MHz): 9.3 (br s, 1H), 8.07 (d, J=1 Hz), 7.34 (m, 2H). MS(CI): 296(M+1).

EXAMPLE 3

6-Chloropyridazino[4,5-b]indole-1,4-dione

To a stirred solution of diethyl 7-chloroindole-2,3-dicarboxylate (0.6 g, 2.0 mM) in ethanol (4 mL) was added hydrazine hydrate (2 mL, 40 mM). The resulting solution was heated to reflux for 3 hrs during which time a white precipitate formed. The solid was filtered, suspended in acetic acid (2 mL), and warmed to reflux for several minutes. The mixture was then cooled to room temperature and the solid filtered and dried. This provided the titled compound as a white solid (0.11 g, 23%), mp >250° C. NMR ($d_6$-DMSO): 12.92 (s, 1H), 11.66 (s, 2H), 8.08 (d, J=8 Hz, 1H), 7.56 (d, J=8 Hz), 7.32 (t, J=8 Hz). MS(CI): 236(M+1).

Analysis for $C_{10}H_6N_3O_2Cl.0.1$ $H_2O$: Calculated: C, 50.59; H, 2.63; N, 17.70; Found: C, 50.41; M, 2.58; N, 17.55.

The starting diethyl 7-chloroindole-2,3-dicarboxylate was prepared made as follows:

a. 2,2'-Dichlorohydrazobenzene

To a stirred solution of 50% NaOH (1 mL, 12.5 mM) was added 2-chloronitrobenzene (3.14 g, 20 mM) and the resulting solution was heated to 60° C. Zinc dust (3 g, 46 mM) was added at such a rate as to keep the temperature of the reaction below 80° C. After the addition was complete, 20% NaOH (6 mL, 30 mM) was added followed by water (10 mL). An additional quantity of zinc dust (4 g, 71 mM) was then added in one portion. The resulting mixture was stirred between 75°–80° C. for 30 minutes. The mixture was cooled to room temperature and the solids were filtered and extracted with ether. The combined filtrates were dried over Na$_2$SO$_4$ and concentrated. Purification via flash column chromatography gave a solid which was then triturated with ether. This afforded the titled product as a yellow solid (1.2 g, 60%). NMR (CDCl$_3$): 7.31 (m, 2H), 7.11 (m, 2H), 6.94 (m, 2H), 6.76 (m, 2H), 6.21 (br s, 2H). MS(CI): 253(M+1).

b. Diethyl 7-Chloroindole-2,3-dicarboxylate

Diethyl acetylenedicarboxylate (1.0 mL, 5.9 mM) was added to a stirred solution of 2,2'-dichlorohydrazobenzene (1.2 g, 6 mM) in methanol (25 mL). The resulting solution was refluxed for 2 hours. The reaction mixture was then cooled to room temperature and concentrated. Purification by flash chromatography afforded material which was then dissolved in diphenyl ether (3 mL) and heated at 200° C. for 2 hrs. The reaction mixture was then cooled to room temperature and purified by flash column chromatography. This afforded the titled compound (0.6 g, 48%) as a red oil. MS(CI): 296(M+1).

EXAMPLE 4

7,9-Dichloropyridazino[4,5-b]indole-1,4-dione

To a stirred solution of diethyl 4,6-dichloroindole-2,3-dicarboxylate (3.22 g, 9.8 mM) in ethanol (20 mL) was added hydrazine hydrate (14.2 mL, 294 mM). The solution was refluxed for 3 hours during which time a precipitate formed. The reaction mixture was then cooled to room temperature, the solid was filtered and heated to reflux in 3N HCl. After several minutes, the mixture was cooled to room temperature and the solid was filtered, washed with ethanol, and dried. This afforded the titled product as a white solid (2.6 g, 90%), mp >300° C. NMR (d$_6$-DMSO): 13.02 (br s, 1H), 11.72 (br s, 2H), 7.54 (s, 1H), 7.40 (s, 1H). MS(CI): 271(M+1).

Analysis for C$_{10}$H$_5$Cl$_2$N$_3$O$_2$.0.4 CH$_3$CH$_2$OH.0.4 H$_2$O: Calculated: C, 43.87; H, 2.80; N, 14.21; Found: C, 43.73; H, 2.81; N, 14.07.

The starting diethyl 4,6-dichloroindole-2,3-dicarboxylate was prepared as follows:

a. 3,3',5,5'-Tetrachlorohydrazobenzene

To a stirred solution of 50% NaOH (20 mL) was added 3,5-dichloronitrobenzene (38.4 g, 200 mM) and the resulting solution was heated at 60° C. Zinc dust (15 g, 230 mM) was added in portions in such a way as to maintain the reaction temperature between 70° and 80° C. The resulting slurry was then diluted with 12 mL of 50% NaOH followed by 35 mL of water. An additional amount of zinc dust (20 g, 310 mM) was added in a single portion and the resulting suspension was heated to 70°–80° C. for 3 hours. The reaction mixture was then cooled to room temperature and the solid obtained was extracted with ethyl acetate. The extracts were dried over Na$_2$SO$_4$ and concentrated to ½ the original volume. An orange solid precipitated which was removed by filtration and discarded. The filtrates were diluted with hexane which caused a precipitate. This was then filtered, providing the titled compound as a yellow solid (11.3 g, 35%). NMR (d$_6$-DMSO): 8.38 (s, 2H), 6.82 (s, 2H), 6.67 (s, 4H). MS(CI): 323(M+1).

b. Diethyl 2-(1,2-di(3,5-Dichloro)phenylhydrazino) maleate

A solution of 3,3',5,5'-tetrachlorohydrazobenzene (11.3 g, 35 mM), diethyl acetylenedicarboxylate (22.4 mL, 140 mM), and ethanol (50 mL) was heated to reflux for 7 hrs. At the end of this time, an additional portion of diethylacetylene dicarboxylate (6 mL, 37.5 mmol) was added and the reaction mixture was refluxed overnight. The solution was then cooled to room temperature and filtered. The filtrate was concentrated to afford an orange oil which was purified by flash column chromatography to afford the titled compound as a white solid (6.4 g, 37%), mp 159°–161° C. NMR (d$_6$-DMSO): 9.59 (s, 1H), 7.50 (s, 3H), 6.97 (s, 1H), 6.82 (s, 2H), 5.29 (s, 1H), 4.16 (q, 2H), 4.03 (q, 2H), 1.16 (t, 6H). MS(CI): 493(M+1).

c. Diethyl 4,6-Dichloroindole-2,3-dicarboxylate

Diethyl 2-(1,2-di(3,5-dichloro)phenylhydrazino)maleate (6.0 g, 12.2 mM) was placed in 20 mL of o-xylene and heated to reflux for one hour. The reaction mixture was then cooled to room temperature and the precipitate was filtered off and washed with hexane. The xylene was then removed which gave an additional precipitate. The precipitates obtained were combined to give the titled product as a white solid (3.17 g, 79%), mp 167°–170° C. MS(CI): 330(M+1).

Analysis for C$_{14}$H$_{13}$Cl$_2$NO$_4$: Calculated: C, 50.93; H, 3.97; N, 4.24; Found: C, 50.99; H, 3.97; N, 4.20.

EXAMPLE 5

7-Bromopyridazino[4,5-b]indole-1,4-dione

To a stirred solution of diethyl 6-bromoindole-2,3-dicarboxylate (0.5 g, 1.47 mM) in ethanol (4 mL) was added hydrazine hydrate (2.2 mL, 44 mM). The solution was heated to reflux for 90 minutes and then cooled to room temperature. The resulting solid was filtered and then suspended in glacial acetic acid (5 mL). After heating this mixture to reflux for several minutes and cooling to room temperature, the solid was filtered off and dried under vacuum. This afforded the titled compound as a white solid (0.35 g, 85%), mp 260° C. NMR (d$_6$-DMSO): 11.81 (br s, 2H), 8.04 (dd, J$_1$=1.0 Hz, J$_2$=8 Hz), 7.76 (s, 1H), 7.46 (d, J=8 Hz), 3.36 (br s, 1H). MS(CI): 280 (M+1).

Analysis for C$_{10}$H$_6$N$_3$O$_2$Br: Calculated: C, 42.88; H, 2.16; N, 15.00; Found: C, 42.46; H, 2.18; N, 15.02.

EXAMPLE 6

9-Bromopyridazino[4,5-b]indole-1,4-dione

To a stirred solution of diethyl 4-bromoindole-2,3-dicarboxylate (0.4 g, 1.2 mM) in ethanol (3 mL) was added hydrazine hydrate (2.0 mL, 40 mM). The mixture was heated to reflux for 2 hours, cooled to room temperature, and the resulting solid was filtered. This was then suspended in glacial acetic acid (3 mL), heated to reflux for several minutes, and cooled to room temperature. The solid was then filtered and dried. This afforded the titled compound as a white solid (0.3 g, 88%), mp >260° C. NMR (d$_6$-DMSO): 12.8 (br s, 1H), 11.52 (br s, 2H), 7.60 (d, J=8 Hz, 1H), 7.52 (d, J=8 Hz, 1H), 7.52 (d, J=8 Hz, 1H), 7.32 (t, J=8 Hz, 1H). MS(CI): 280(M+1).

Analysis for C$_{10}$H$_6$BrN$_3$O$_2$.0.4 H$_2$O: Calculated: C, 41.81; H, 2.34; N, 14.63; Found: C, 41.80; H, 2.38; N, 14.67.

The starting diethyl 4-bromoindole-2,3-dicarboxylate and 6-bromoindole-2,3-dicarboxylate were prepared as follows:

a. 3,3'-Dibromohydrazobenzene

To a stirred solution of 50% NaOH (3.6 mL, 45 mM) was added 3-bromonitrobenzene (15 g, 74 mM) and the resulting solution was heated to 60° C. Zinc dust (11 g, 170 mM) was added in portions in such a manner as to keep the reaction temperature below 80° C. After the addition was complete, 20% NaOH (22 mL, 113 mM) was added followed by water (37 mL). An additional portion of zinc dust (14 g, 220 mM) was then added in one portion. The resulting mixture was heated at 70° C. for 1 hour, cooled to room temperature, and poured into ether (200 mL). The liquid was decanted away from the solids and the solids were resuspended in ether and this procedure was repeated an additional three times. The organic layers were combined, dried over Na$_2$SO$_4$, and concentrated. Purification by flash column chromatography afforded the titled compound as a white solid (10.1 g, 79%). NMR (CDCl$_3$): 6.99 (m, 6H), 6.76 (dd, J$_1$=1 Hz, J$_2$=8 Hz), 5.66 (br s, 2H). MS(CI): 341/343(M+1).

b. Diethyl 4-Bromoindole-2,3-dicarboxylate and Diethyl 6-Bromoindole-2,3-dicarboxylate Diethylacetylene dicarboxylate (1.2 g, 7 mM) was added to a stirred solution of 3,3'-dibromohydrazobenzene (2.0 g, 5.9 mM) in methanol (6 mL). The resulting solution was then refluxed for 90 minutes, cooled to room temperature, concentrated, and purified by flash chromatography. This afforded a yellow oil (2.4 g) which was then dissolved in diphenyl ether (5 mL) and heated to 210° C. for two hours. The reaction mixture was then cooled to room temperature and then applied directly to a flash silica gel column. Elution with methylene chloride afforded a mixture of the bromo isomers as yellow oil which were separated by flash column chromatography. This provided diethyl 6-bromoindole-2,3-dicarboxylate (1.1 g, 69%) as a white solid and diethyl 4-bromoindole-2,3-dicarboxylate (0.4 g, 25%) as a yellow solid. NMR (d$_6$-DMSO): Diethyl 6-bromoindole-2,3-dicarboxylate: 9.29 (br s, 1H), 7.92 (d, J=9.0, 1H), 7.61 (d, J=2 Hz, 1H), 7.36 (dd, J1=9 Hz, J2=2 Hz, 1H), 4.45 (m, 4H), 1.44 (m, 6H). Diethyl 4-bromoindole-2,3-dicarboxylate: 9.12(br s,1H), 7.39 (d, J=8 Hz, 2H), 7.20 (t, J=8 Hz, 1H), 4.48 (q, J=7 Hz, 2H), 4.41 (q, J=7 Hz, 2H), 1.42 (m, 6H). MS(CI): 6-bromo isomer, 340/342(M+1); 4-bromo isomer, 340/342(M+1).

EXAMPLE 7

7,9-Ditrifluoromethylpyridazino[4,5-b]indole-1,4-dione

Using a procedure similar to that described in example 1, except starting with diethyl 4,6-ditrifluoromethylindole-2,3-dicarboxylate as starting material, the title compound was obtained in 73% yield as a white solid, mp >260° C.

Analysis for $C_{12}H_5N_3O_2F_6 \cdot 0.4\ H_2O$: Calculated: C, 41.85; H, 1.70; N, 12.20; Found: C, 41.59; H, 1.86; N, 12.25.

The starting diethyl 4,6-ditrifluoromethylindole-2,3-dicarboxylate was prepared as follows:

a. 3,3',5,5'-Tetratrifluoromethylhydrazobenzene

Using a procedure similar to that described in example 1a, except starting with 3,5-ditrifluoromethylnitrobenzene, the titled compound was obtained as a yellow solid in 72% yield. MS(CI): 457(M+1).

b. Diethyl 4,6-Ditrifluoromethylindole-2,3-dicarboxylate

Using a procedure described in example 1b, except using 3,3',5,5'-tetratrifluoromethylhydrazobenzene as starting material, the titled compound was obtained as a yellow oil. NMR (CDCl$_3$): 9.74 (br s, 1H), 7.95 (s, 1H), 7.78 (s, 1H), 4.46 (m, 4H), 1.39 (m, 6H). MS(CI): 398(M+1).

EXAMPLE 8

7-Methoxypyridazino[4,5-b]indole-1,4-dione

Using a procedure similar to that described in example 1, except starting with diethyl 6-methoxyindole-2,3-dicarboxylate, the titled compound was obtained in 45% yield as a white solid, mp >260° C.

Analysis for $C_{11}H_9N_3O_3 \cdot 0.1\ H_2O$: Calculated: C, 56.70; H, 3.98; N, 18.03; Found: C, 56.68; H, 4.00; N, 17.88.

EXAMPLE 9

9-Methoxypyridazino[4,5-b]indole-1,4-dione

Using a procedure similar to that described in example 1, except starting with diethyl 4-methoxyindole-2,3-dicarboxylate, the titled compound was prepared in 53% as a white solid, mp >260° C.

Analysis for $C_{11}H_9N_3O_3 \cdot 0.6\ H_2O \cdot 0.3\ CH_3CO_2H$: Calculated: C, 53.21; H, 4.47; N, 16.05; Found: C, 53.27; H, 4.50; N, 16.10.

The starting diethyl 4-methoxyindole-2,3-dicarboxylate and diethyl 6-methoxy-2,3-dicarboxylate could be prepared as follows:

a. 3,3'-Dimethoxyhydrazobenzene

Using a procedure similar to that described in example 1.1, except starting with 3-nitroanisole, the titled compound was obtained in 65% yield as a yellow oil. MS(CI): 245 (M+1).

b. Diethyl 4-Methoxyindole-2,3-dicarboxylate and Diethyl 6-Methoxyindole-2,3-dicarboxylate Using a procedure similar to that described in example 1b, except starting with 3,3'-dimethoxyhydrazobenzene, the titled compounds were obtained in 34% and 38% yield, respectively. Diethyl 4-methoxyindole-2,3-dicarboxylate: NMR (d$_6$-DMSO): 8.89 (br s, 1H), 7.26 (t, J=8 Hz, 1H), 6.99 (d, J=8 Hz, 1H), 6.53 (d, J=8 Hz, 1H), 3.90 (s, 3H), 4.42 (m, 4H), 1.41 (m, 6H). MS(CI): 292(M+1). Diethyl 6-methoxyindole-2,3-dicarboxylate: NMR (d$_6$-DMSO): 9.11 (br s, 1H), 7.91 (d, J=9 Hz, 1H), 6.91 (d, J=9 Hz, 1H), 6.83 (s, 1H), 4.42 (m, 4H), 3.91 (s, 3H), 1.41 (m, 6H). MS(CI): 292(M+1).

EXAMPLE 10

7,9-Dimethylpyridazino[4,5-b]indole-1,4-dione

Using a procedure similar to that described in example 1, except starting with diethyl 4,6-dimethylindole-2,3-dicarboxylate, the titled compound was obtained 68% yield as a white solid, mp >250° C.

Analysis for $C_{12}H_{11}N_3O_2 \cdot 0.15\ H_2O$: Calculated: C, 62.14; H, 4.91; N, 18.12; Found: C, 62.34; H, 5.01; N, 18.02.

The starting diethyl 4,6-dimethylindole-2,3-dicarboxylate was prepared as follows:

a. 3,3',5,5'-Tetramethylhydrazobenzene

Using a procedure similar to that described in example 1a, except using 3,5-dimethylnitrobenzene as starting material, the titled compound was obtained in 33% yield. MS(CI): 241(M+1).

b. Diethyl 4,6-Dimethylindole-2,3-dicarboxylate

Using a procedure similar to that described in example 1b, except using 3,3',5,5'-tetramethylhydrazobenzene as starting material, the titled compound was obtained in 51% yield as a yellow solid. NMR (CDCL$_3$): 8.8 (br s, 1H), 7.02 (br s, 1H), 6.80 (s, 1H), 4.42 (m, 2H), 2.48 (s, 3H), 2.41 (s, 3H), 1.40 (m, 6). MS(CI): 290(M+1).

EXAMPLE 11

6-Methoxypyridazino[4,5-b]indole-1,4-dione

Using a procedure similar to that described in example 1, except using diethyl 7-methoxyindole-2,3-dicarboxylate as starting material, the titled product was obtained in 69% yield as a white solid, mp >260° C.

Analysis for $C_{11}H_9N_3O_3 \cdot 0.4\ H_2O \cdot 0.4\ CH_3COOH$: Calculated: C, 54.01; H, 4.38; N, 16.01; Found: C, 54.05; H, 4.42; N, 16.15.

The starting diethyl 7-methoxyindole-2,3-dicarboxylate was be prepared as follows:

a. 2,2'-Dimethoxyhydrazobenzene

Using a procedure similar to that described in example 1a, except using 2-nitroanisole as starting material, the titled compound was obtained in 46% yield as an oil. MS(CI): 245(M+1).

b. Diethyl 7-Methoxyindole-2,3-dicarboxylate

Using a procedure similar to that described in example 1b, except using 2,2'-dimethoxyhydrazobenzene, the titled compound was obtained in 7% yield. MS(CI): 292(M+1).

EXAMPLE 12

7-Iodopyridazino[4,5-b]indole-1,4-dione

Using a procedure similar to that used in example 1, except using diethyl 6-iodoindole-2,3-dicarboxylate as starting material, the titled compound was obtained in 51% yield as a white powder, mp >250° C.

Analysis for $C_{10}H_6N_3O_2I$: Calculated: C, 36.72; H, 1.85; N, 12.85; Found: C, 36.35; B, 2.10; N, 12.77.

The starting diethyl 6-iodoindole-2,3-dicarboxylate could be prepared as follows:

a. 3,3'-Diiodohydrazobenzene

Using a procedure similar to that described in example 1a, except using 3-iodonitrobenzene as starting material, the desired product was obtained in 91% yield. MS(CI): 388 (M+1).

b. Diethyl 6-Iodoindole-2,3-dicarboxylate

Using a procedure similar to that described in example 1b, except using 3,3'-diiodohydrazobenzene as starting material, the titled compound was obtained in 12% yield as a white solid. NMR: (CDCl$_3$): 7.58 (m, 2H), 7.52 (d, 1H), 4.44 (m, 4H), 1.41 (m, 6H) MS(CI): 388(M+1).

EXAMPLE 13

7-Trifluoromethylpyridazino[4,5-b]indole-1,4-dione

Using a procedure similar to that described in example 1, except using diethyl 6-trifluromethylindole-2,3-dicarboxylate as starting material, the titled compound was obtained in 73% yield as a white solid, mp 291°–293° C.

Analysis for $C_{11}H_6N_3O_2F_3.0.4\ CH_3COOH.0.3\ H_2O$ Calculated: C, 47.46; H, 2.77; N, 14.07; Found: C, 47.53; H, 2.61; N, 13.68.

The starting diethyl 6-trifluoromethylindole-2,3-dicarboxylate was prepared as follows:

a. 3,3'-Ditrifluoromethylhydrazobenzene

Using a procedure similar to that described in Example 1.1, except using 3-nitro-α,α,α-trifluorotoluene as starting material, the titled compound was obtained as a yellow oil in quantitative yield.

b. Diethyl 7-Trifluoromethylindole-2,3-dicarboxylate

Using a procedure similar to that described in Example 1b, except using 3,3'-ditrifluoromethylhydrazobenzene as starting material, the desired product was obtained in 44% yield. NMR (d$_6$-DMSO): 9.42 (br s, 1H), 8.19 (d, J=9 Hz, 1H), 7.74 (s, 1H), 7.49 (d, J=9 Hz, 1H), 4.48 (m, 4H), 1.45 (m, 6H). MS(CI): 330(M+1).

EXAMPLE 14

7,9-Dibromopyridazino[4,5-b]indole-1,4-dione

Using a procedure similar to that described in example 1, except using diethyl 4,6-dibromoindole-2,3-dicarboxylate as starting material, the titled compound was obtained in 38% yield as a white solid, mp >400° C.

Analysis for $C_{10}H_5N_3O_2Br_2.1.0\ CH_3COOH$: Calculated: C, 34.39; M, 2.16; N, 10.02; Found: C, 34.36; H, 2.24; N, 9.64.

The starting diethyl 4,6-dibromoindole-2,3-dicarboxylate was prepared as follows:

a. 3,3',5,5'-Tetrabromohydrazobenzene

Using a procedure similar to that described in example 1a, except using 3,5-dibromonitrobenzene as starting material, the titled product was obtained as in 74% yield as a dark yellow oil. MS(CI): 499(M+1).

b. Diethyl 4,6-Dibromoindole-2,3-dicarboxylate

Using a procedure similar to that described in example 1b, except using 3,3',5,5'-tetrabromohydrazobenzene as starting material, the titled compound was obtained in 48% yield as a yellow oil. MS(CI): 419 (M+1).

EXAMPLE 15

9-Chloropyridazino[4,5-b]indole-1,4-dione

Using a procedure similar to that described in example 1, except using diethyl 4-chloroindole-2,3-dicarboxylate as starting material, the title compound was obtained in 83% yield as a white solid.

Analysis for $C_{10}H_6N_3O_2Cl.0.5\ CH_3COOH.0.5\ H_2O$: Calculated: C, 48.10; H, 3.30; N, 15.30; Found: C, 48.41; H, 3.21; N, 15.19.

EXAMPLE 16

7-Chloro-8-methoxypyridazino[4,5-b]indole-1,4-dione

To a solution of ethanol (15 ml) and dimethyl 5-methoxy-6-chloroindole-2,3-dicarboxylate (0.67 g, 2.30 mM), was added hydrazine hydrate (3.45 g, 0.69 mM). The resulting heterogeneous mixture was refluxed for 5 hr and then cooled to room temperature. The ethanol was removed under reduced pressure, acetic acid (15 ml) was added, and the resulting mixture refluxed for 2 hr. The reaction was cooled to room temperature, filtered, and dried. This afforded the titled compound as a white solid (0.18 g, 30%).

NMR (d$_6$-DMSO): 12.52 (bs,1H), 11.71 (bs,2H), 7.65 (s,1H), 7.62 (s,1H), 3.93 (s,3H). MS(CI): 266 (M+1). Analysis for $C_{11}H_8N_3O_3Cl.1.0\ CH_3COOH$: Calculated: C, 47.94; H, 3.71; N, 12.90; Found: C, 47.86; H, 3.75; N, 12.56.

The starting dimethyl 5-methoxy-6-chloroindole-2,3-dicarboxylate was prepared as follows:

a. 2,2'-Dichloro-3,3'-dimethoxyhydrazobenzene

To a stirred solution of THF (30 ml) and 2-chloro-3-methoxynitrobenzene (10 g, 53.3 mM), was added 50% NaOH (2.5 ml, 62.5 mM) and the resultant solution was heated to 65° C. Zinc dust (8.0 g, 0.12 mM) was added by portions, ensuring that reaction temperature remained below 70° C. Following the addition, the reaction was maintained at 65° C. for 30 minutes. To this mixture was added 10% NaOH (40 ml, 0.1M) and additional zinc dust (10.5 g, 0.16M). The resulting mixture was stirred at 65° C. for 3 hours and then cooled to room temperature. Ether (100 ml) was then added, the mixture stirred, and the ether decanted. This procedure was repeated twice. The ether fractions were combined and dried over MgSO$_4$, filtered, and the solvent was concentrated under reduced pressure. This afforded the titled compound as a solid in quantitative yield and was used in the next step without further purification.

MS(CI): 313 (m+1).

b. Dimethyl 5-Methoxy-6-chloroindole-2,3-dicarboxylate

To a solution of ethanol (50 ml) and 2,2'-dichloro-3,3'-dimethoxyhydrazobenzene (8.34 g, 26.7 mM) was added dimethylacetylene dicarboxylate (5.69 g, 40.0 mM). The resulting solution was refluxed for 24 hr and then cooled to room temperature. The ethanol was removed under reduced pressure, xylene (50 ml) added, and the subsequent solution was refluxed for 18 hr. The reaction mixture was then cooled to room temperature and the xylene removed under reduced pressure. Purification by flash chromatography (1:1 EtOAc/Hexane), yielded two regioisomers as solids (2.04 g, 26%).

Dimethyl 5-methoxy-4-chloroindole-2,3-dicarboxylate: MS(CI): 298 (M+1).

Dimethyl 5-methoxy-6-chloroindole-2,3-dicarboxylate: NMR(CDCl$_3$): 9.27 (bs,1H), 7.55 (s,1H), 7.48 (s,1H), 3.98 (s,6H), 3.97 (s,3H). MS(CI): 298 (M+1).

EXAMPLE 17

7-Bromo-8-methoxypyridazino[4,5-b]indole-1,4-dione

Using a procedure similar to that described in example 1, except using dimethyl 5-methoxy-6-bromoindole-2,3-dicarboxylate as starting material, the titled compound was obtained as a white solid (0.42 g, 62%).

NMR (d$_6$-DMSO): (partial) 7.78 (s,1H), 7.63 (s,1H), 3.92 (s,3H). MS(CI): 310 (M+1). Analysis for $C_{11}H_8N_3O_3Cl.1.0$ $CH_3COOH.0.2$ $H_2O$: Calculated: C, 41.78; H, 3.34; N, 11.24; Found: C, 41.81; H, 3.12; N, 11.26.

The starting dimethyl 5-methoxy-6-bromoindole-2,3-dicarboxylate was prepared as follows:

a. 2,2'-Dibromo-3,3'-dimethoxyhydrazobenzene

Using a procedure similar to that described in example 1a, except using 2-bromo-3-methoxynitrobenzene as starting material, the titled compound was obtained (8.41 g, 97%) and used without further purification.

MS(CI): 401(m+1).

b. Dimethyl 5-Methoxy-6-bromoindole-2,3-dicarboxylate

Using a procedure similar to that described in example 1b, except using 2,2'-dibromo-3,3'-dimethoxyhydrazobenzene as starting material, the two desired regioisomers were obtained (1.50 g, 18%). Purification was effected by flash chromatography (40% EtOAc/Hexane).

Dimethyl 5-methoxy-4-bromoindole-2,3-dicarboxylate: MS(CI): 342 (M+1).

Dimethyl 5-methoxy-6-bromoindole-2,3-dicarboxylate: NMR(CDCL$_3$): 9.21 (bs,1H), 7.65 (s,1H), 7.52 (s,1H), 3.97 (s,6H), 3.95 (s,3H). MS(CI): 342 (M+1).

EXAMPLES 18–33

The following Examples were made generally as set forth in Example 1, using appropriate corresponding precursors to make the compounds listed.

TABLE 1

Pyridexino[4,5-b]indole-1,4-diones synthesized via the procedure described in Example 1

| Ex. # | Name | Yield | m.p. | MS(CI) | NMR(d6-DMSO) | Analysis(experimental/theory) |
|---|---|---|---|---|---|---|
| 18 | 7,9-Dichloro-8-methoxypyridazino[4,5-b]indole-1,4-dione | Quant | >370-d | 300(M+1) | (partial)3.84(s, 3H), 7.62(s, 1H) | C=42.74/42.83, H=2.61/2.81, N=13.59/13.26 $C_{11}H_7N_3O_3Cl_2.0.8H_2O$ |
| 19 | 6-Methoxy-9-trifluoromethylpyridazino[4,5-b]indole-1,4-dione | 19% | >250 | 300(M+1) | 4.04(s, 3H), 7.12(d, 1H, J=8Hz), 7.66(d, 1H, J=8Hz), 11.40(brs, 2H). | C=48.03/48.17, H=2.68/2.69, N=14.09/14.04 $C_{12}H_8N_3O_3F_3$ |
| 20 | 7,9-Dichloro-6-methoxypyridazino[4,5-b]indole-1,4-dione | 43% | 360-d | 300(M+1) | 3.92(s, 3H), 7.41(s, 1H), 11.60(brs, 2H), 13.29(brs, 1H) | C=41.62/41.53, H=2.92/2.85, N=13.24/13.21 $C_{11}H_7N_3O_3Cl_2.1.0H_2O$ |
| 21 | 7,8-Dichloropyridazino[4,5-b]indole-1,4-dione | 63% | >400 | 270(M+1) | 7.80(s, 1H), 8.21(s, 1H), 11.71(brs, 2H), 12.52(brs, 1H). | C=44.33/44.47, H=2.10/1.87, N=15.33/15.56 N=15.33/15.56 $C_{10}H_5N_3O_2Cl_2$ |
| 22 | 8,9-Dichloropyridazino[4,5-b]indole-1,4-dione | quant | >400 | 270(M+1) | (partial)7.56(d, 1H, J=9Hz), 7.64(d, 1H, J=9Hz). | C=42.52/42.22, H=2.59/2.34, N=14.50/14.77 $C_{10}H_5N_3O_2Cl_2.0.8H_2O$ |
| 23 | 9-Trifluoromethylpyridazino[4,5-b]indole-1,4-dione | 56% | 387–390 | 270(M+1) | 7.63(t, 1H, J=8Hz), 7.74(d, 1H, J=8Hz), 7.96(d, 1H, J=8Hz), 11.50(brs, 2H), 13.09(brs, 1H). | C=46.44/46.59, H=2.66/2.70, N=14.82/14.92 $C_{11}H_6N_3O_2F_3.0.8H_2O$ |
| 24 | 7-Methoxy-9-trifluoromethylpyridazino[4,5-b]indole-1,4-dione | 86% | 345–350-d | 300(M+1) | (partial)4.02(s, 3H), 7.01(s, 1H), 7.41(s, 1H). | C=47.15/47.31, H=3.09/2.95, N=13.29/13.35. $C_{12}H_8N_3O_3F_3.0.2H_2O.0.2HOAc$ |
| 25 | 7-Trifluoromethyl-9-methoxypyridazino[4,5-b]indole-1,4-dione | quant | 389–392 | 300(M+1) | 3.91(s, 3H), 7.30(m, 2H), 11.51(brs, 2H), 12.80(brs, 1H). | C=45.39/45.44, H=3.27/3.18, N=13.22/13.25 $C_{12}H_8N_3O_3F_3.1.0H_2O$ |
| 26 | 7-Trifluoromethyl-9-chloropyridazino[4,5-b]indole-1,4-dione | 68% | 393–396-d | 304(M+1) | 7.64(s, 1H), 7.84(s, 1H), 11.79(brs, 2H) 13.33(brs, 1H). | C=43.07/43.26, H=2.16/2.03, N=12.74/12.82. $C_{11}H_5N_3O_2ClF_3.0.4HOAc$ |
| 27 | 9-Methylpyridazino[4,5-b]indole-1,4-dione | 60% | 370–375-d | 216(M+1) | 2.99(s, 3H), 7.04(d, 1H, J=6Hz), 7.33(t, 1H, J=6Hz), 7.41(d, 1H, J=7Hz), 11.48(brs, 2H), 12.47(brs, 1H) | C=59.46/59.40, H=4.46/4.44, N=18.96/18.89. $C_{11}H_9N_3O_2.0.4H_2O$ |
| 28 | 7-Methylpyridazino[4,5-b]indole-1,4-dione | 67% | 368–372-d | 216(M+1) | 2.47(s, 3H), 7.13(d, 1H, J=8Hz), 7.38(s, 1H), 7.97(d, 1H, J=8Hz), 11.50(brs, 2H), 12.41(brs, 1H) | C=58.55/58.46, H=4.25/4.55, N=18.55/18.59. $C_{11}H_{13}N_3O_2.0.6H_2O$ |

TABLE 1-continued

Pyridexino[4,5-b]indole-1,4-diones synthesized via the procedure described in Example 1

| Ex. # | Name | Yield | m.p. | MS(CI) | NMR(d6-DMSO) | Analysis(experimental/theory) |
|---|---|---|---|---|---|---|
| 29 | 7,9-Dimethyl-8-methoxypyridazino[4,5-b]indole-1,4-dione | 45% | >385-d | 260(M+1) | (partial)2.36(s, 3H), 2.95(s, 3H), 3.67(s, 3H), 7.23(s, 1H), | C=58.47/58.60, H=5.18/5.22, N=15.49/15.77 $C_{13}H_{13}N_3O_3.0.4H_2O$ |
| 30 | 7,9-Dichloro-8-ethoxypyridazino[4,5-b]indole-1,4-dione | 37% | >388-d | 314(M+1) | (partial)1.41(t, 3H), J=7Hz), 4.04 (q, 2H, J=7Hz), 7.61(s, 1H) | C=45.15/45.11, H=3.05/3.03, N=13.03/13.15 $C_{12}H_9N_3O_3Cl_2.0.3H_2O$ |
| 31 | 7-Methyl-8-methoxy-9-chloropyridazino[4,5-b]indole-1,4-dione | 76% | >380-d | 280(M+1) | 2.40(s, 3H), 3.76(s, 3H), 7.36(s, 1H), 11.56(brs, 2H), 12.66(brs, 1H). | C=50.41/50.23, H=3.85/3.88, N=13.57/13.94 $C_{12}H_{10}N_3O_3Cl.0.2H_2O.0.3HOAc$ |
| 32 | 9-Ethenylpyridazino[4,5-b]indole-1,4-dione | 81% | >360-d | 228(M+1) | 5.30(d, 1H, J=12Hz), 5.88(d, 1H, J=18Hz), 7.44(t, 1H, J=8Hz), 7.52(d, 1H, J=8Hz), 7.63(d, 1H, J=7Hz), 8.92(m, 1H), 11.58(brs, 2H), 12.54(brs, 1H). | C=60.56/60.32, H=4.37/4.34, N=17.53/17.58 $C_{12}H_9N_3O_2.0.65H_2O$ |
| 33 | 9-Ethylpyridazino[4,5-b]indole-1,4-dione | 56% | 360–365-d | 230(M+1) | 1.21(t, 3H, J=7.4Hz), 3.50(q, 2H, J=7.5Hz), 7.08(d, 1H, J=6.9Hz), 7.40(m, 2H), 11.47(brs, 2H), 12.46(brs, 1H). | C=62.14/61.96, H=4.88/4.93, N=17.95/18.05 $C_{12}H_{11}N_3O_2.0.2H_2O$ |

EXAMPLE 34

The following illustrate representative pharmaceutical dosage forms containing a compound of formula I, for example as illustrated in any of the previous Examples, (hereafter referred to as "compound X"), for therapeutic or prophylactic use in humans:

| (a) Tablet | mg/tablet |
|---|---|
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |

| (b) Capsule | |
|---|---|
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

EXAMPLE 35

The following illustrates a representative parenteral dosage form containing a compound of formula I, referred to as "Compound X":

| Parenteral Formulation: | mg/mL |
|---|---|
| Compound | 2.0 |
| Meglumine | 19.5 |
| Dextrose, anhydrous | 39.5 |
| Sterile Water for Injection | qs ad 1 mL |

The solution is prepared by conventional measures well known in the pharmaceutical field.

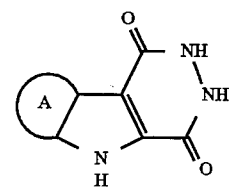

I

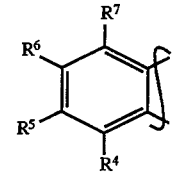

Ia

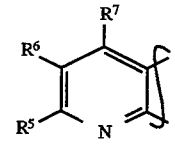

Ib

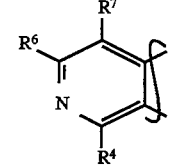

Ic

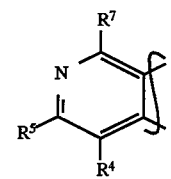

Id

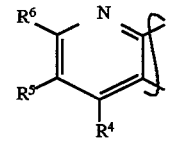

Ie

-continued
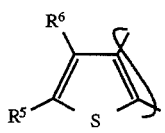 If
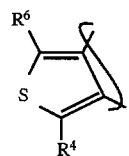 Ig
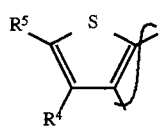 Ih
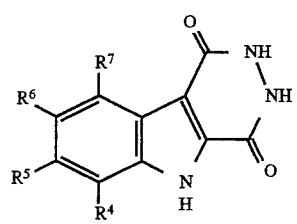 IIa
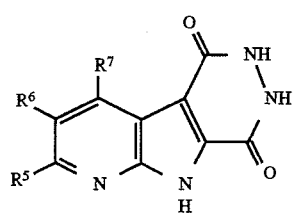 IIb
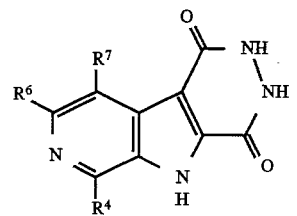 IIc
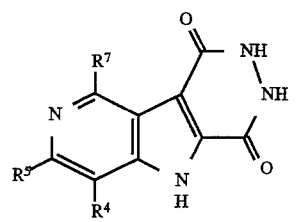 IId
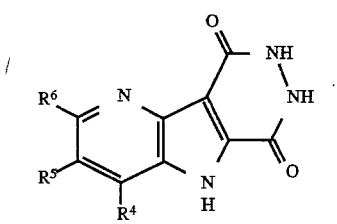 IIe
-continued
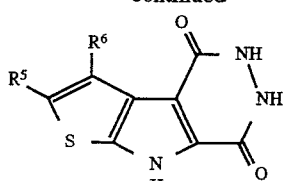 IIf
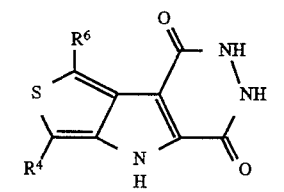 IIg
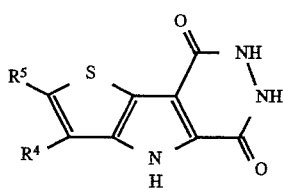 IIh
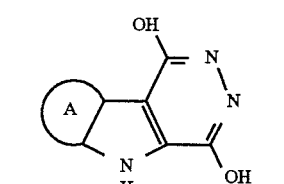 IIIa
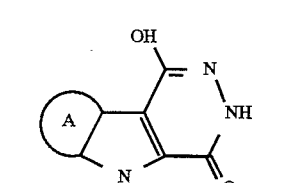 IIIb
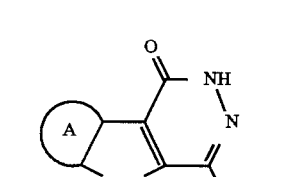 IIIc
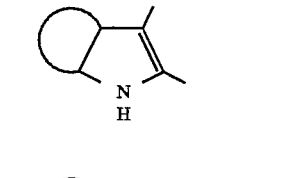 IV
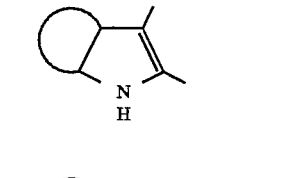 V -continued

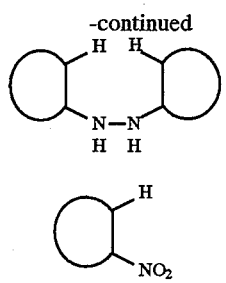

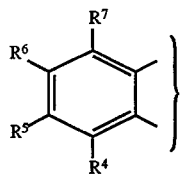

What is claimed is:
1. A compound of formula I

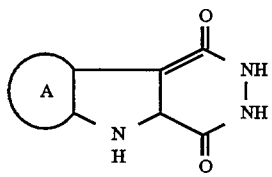

or a pharmaceutically acceptable salt thereof, wherein Ring A is formula Ia,

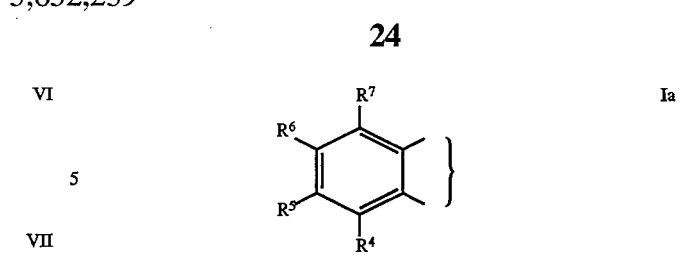

wherein $R^4$, $R^5$, $R^6$, and $R^7$ are independently selected from the group consisting of hydrogen, halo, ethenyl, prop-1-enyl, prop-2-enyl, ethynyl, prop-1-ynyl, prop-2-ynyl, but-2-enyl, (1–3C)perfluoroalkyl, (1–3C)alkyl substituted with trifluoromethyl, nitro, hydroxy, methoxy, ethoxy, $CO_2R^b$, $CONHR^b$, $CONR_2^b$, CN, and cyclopropyl, wherein $R^b$ is selected from hydrogen and (1–4C)alkyl;

but excluding compounds wherein, when ring A has formula Ia, $R^4$-$R^7$ are each hydrogen.

2. A compound according to claim 1 which is selected from:
7,9-dichloro-8-methoxypyridazino[4,5-b]indole-1,4-dione;
7,9-dichloropyridazino[4,5-b]indole-1,4-dione;
7-trifluoromethylpyridazino[4,5-b]indole-1,4-dione;
7-bromopyridazino[4,5-b]indole-1,4-dione;
7-chloropyridazino[4,5-b]indole-1,4-dione;
7-iodopyridazino[4,5-b]indole-1,4-dione;
7,9-dibromopyridazino[4,5-b]indole-1,4-dione;
7-methoxypyridazino[4,5-b]indole-1,4-dione;
6-methoxypyridazino[4,5-b]indole-1,4-dione; and
7,9-ditrifluoromethylpyridazino[4,5-b]indole-1,4-dione.

3. A pharmaceutical composition suitable for the treatment of ischemia, stroke, hypoglycemia, anoxia and epilepsy comprising an effective amount of a compound of formula I

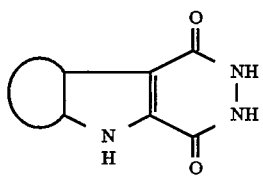

or a pharmaceutically acceptable salt thereof, wherein ring A is formula Ia,

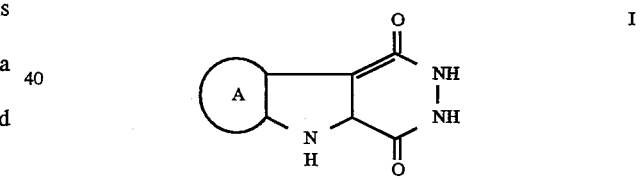

wherein $R^4$, $R^5$, $R^6$, and $R^7$ are independently selected from the group consisting of hydrogen, halo, ethenyl, prop-1-enyl, prop-2-enyl, ethynyl, prop-1-ynyl, prop-2-ynyl, but-2-enyl, (1–3C)perfluoroalkyl, (1–3C)alkyl substituted with trifluoromethyl, nitro, hydroxy, methoxy, ethoxy, $CO_2R^b$, $CONHR^b$, $CONR_2^b$, CN, and cyclopropyl, wherein $R^b$ is selected from hydrogen and (1–4C)alkyl; but excluding compounds wherein, when ring A has formula Ia, $R^4$-$R^7$ are each hydrogen; and a pharmaceutically acceptable diluent or carrier wherein the composition is utilized to antagonize an NMDA receptor in humans.

4. A pharmaceutical composition according to claim 3 comprising a compound selected from:
7,9-dichloro-8-methoxypyridazino[4,5-b]indole-1,4-dione;
7,9-dichloropyridazino[4,5-b]indole-1,4-dione;
7-trifluoromethylpyridazino[4,5-b]indole-1,4-dione;
7-bromopyridazino[4,5-b]indole-1,4-dione;
7-chloropyridazino[4,5-b]indole-1,4-dione;
7-iodopyridazino[4,5-b]indole-1,4-dione;
7,9-dibromopyridazino[4,5-b]indole-1,4-dione;
7-methoxypyridazino[4,5-b]indole-1,4-dione;
6-methoxypyridazino[4,5-b]indole-1,4-dione; and
7,9-ditrifluoromethylpyridazino[4,5-b]indole-1,4-dione and a pharmaceutically acceptable carrier or diluent.

5. A method of treating ischemia, stroke, hypoglycemia, anoxia and epilepsy comprising administering to an animal in need of such treatment an effective amount of a compound of formula I

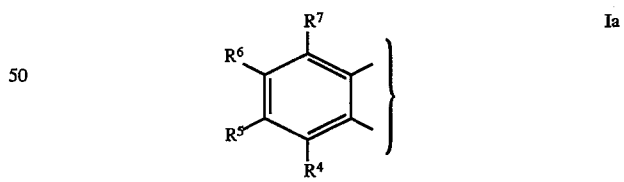

or a pharmaceutically acceptable salt thereof, wherein ring A is formula Ia,

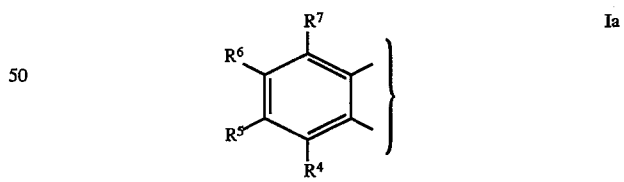

wherein $R^4$, $R^5$, $R^6$, and $R^7$ are independently selected from the group consisting of hydrogen, halo, (1–4C)alkyl which may contain a double or triple bond; (1–3C)perfluoroalkyl, (1–3C)alkyl substituted with trifluoromethyl, nitro, hydroxy, methoxy, ethoxy, $CO_2R^b$, $CONHR^b$, $CONR_2^b$, CN, and cyclopropyl, wherein $R^b$ is selected from hydrogen and (1–4C)alkyl.

6. A method as claimed in claim 5 wherein said compound is selected from:
7,9-dichloro-8-methoxypyridazino[4,5-b]indole-1,4-dione;
7,9-dichloropyridazino[4,5-b]indole-1,4-dione;
7-trifluoromethylpyridazino[4,5-b]indole-1,4-dione;
7-bromopyridazino[4,5-b]indole-1,4-dione;

7-chloropyridazino[4,5-b]indole-1,4-dione;
7-iodopyridazino[4,5-b]indole-1,4-dione;
7,9-dibromopyridazino[4,5-b]indole-1,4-dione;
7-methoxypyridazino[4,5-b]indole-1,4-dione;
6-methoxypyridazino[4,5-b]indole-1,4-dione; and
7,9-ditrifluoromethylpyridazino[4,5-b]indole-1,4-dione.

7. A method of treating stroke according to claim 5.

* * * * *

UNITED STATES PATENT AND TRADEMARK OFFICE
CERTIFICATE OF CORRECTION

PATENT NO. : 5,652,239
DATED : JULY 29, 1997
INVENTOR(S) : THOMAS M. BARE ET AL.

It is certified that error appears in the above-identified patent and that said Letters Patent is hereby corrected as shown below:

Column 22, line 55, formula IV which reads as:

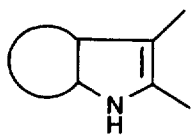

should read as:

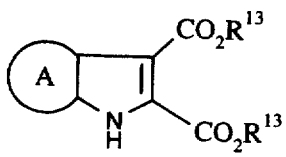

Column 22, line 60, formula V which reads as:

UNITED STATES PATENT AND TRADEMARK OFFICE
CERTIFICATE OF CORRECTION

PATENT NO. : 5,652,239
DATED : JULY 29, 1997
INVENTOR(S) : THOMAS M. BARE ET AL.

It is certified that error appears in the above-identified patent and that said Letters Patent is hereby corrected as shown below:

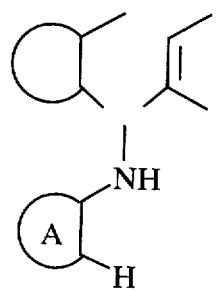

should read as:

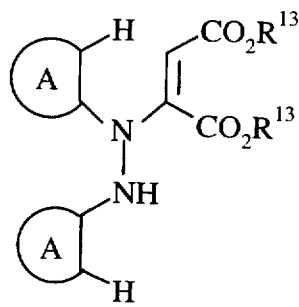

Column 23, line 5, Formula VI which reads as:

UNITED STATES PATENT AND TRADEMARK OFFICE
CERTIFICATE OF CORRECTION

PATENT NO. : 5,652,239
DATED : JULY 29, 1997
INVENTOR(S) : THOMAS M. BARE ET AL.

It is certified that error appears in the above-identified patent and that said Letters Patent is hereby corrected as shown below:

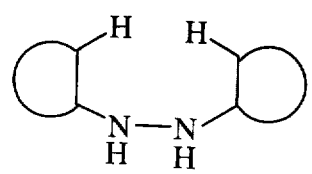

should read as:

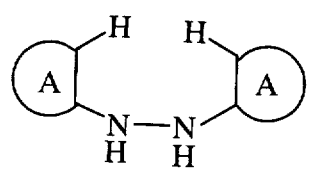

Column 23, line 10, formula VII which reads as:

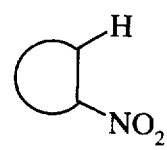

should read as:

UNITED STATES PATENT AND TRADEMARK OFFICE
CERTIFICATE OF CORRECTION

PATENT NO. : 5,652,239
DATED : JULY 29, 1997
INVENTOR(S) : THOMAS M. BARE ET AL.

It is certified that error appears in the above-identified patent and that said Letters Patent is hereby corrected as shown below:

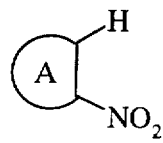

Column 23, claim 1, line 20, formula I which reads as:

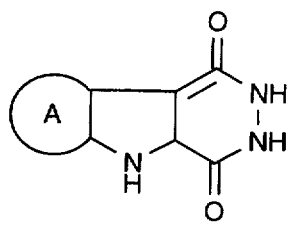

should read as:

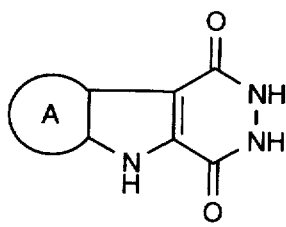

UNITED STATES PATENT AND TRADEMARK OFFICE
CERTIFICATE OF CORRECTION

PATENT NO. : 5,652,239

DATED : JULY 29, 1997

INVENTOR(S) : THOMAS M. BARE ET AL.

It is certified that error appears in the above-identified patent and that said Letters Patent is hereby corrected as shown below:

Column 23, claim 3, line 60, formula I which reads as:

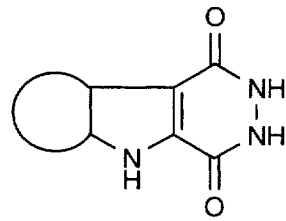

should read as

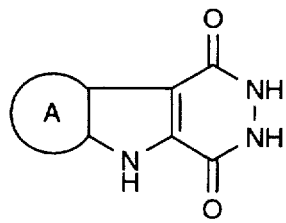

Column 24, claim 5, line 40, formula I which reads as:

UNITED STATES PATENT AND TRADEMARK OFFICE
CERTIFICATE OF CORRECTION

PATENT NO. : 5,652,239
DATED : JULY 29, 1997
INVENTOR(S) : THOMAS M. BARE ET AL.

It is certified that error appears in the above-identified patent and that said Letters Patent is hereby corrected as shown below:

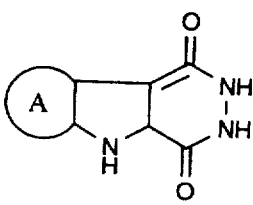

should read as:

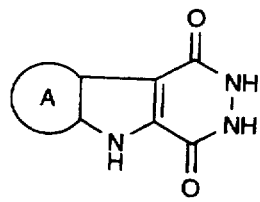

Signed and Sealed this

Thirtieth Day of December, 1997

Attest:

BRUCE LEHMAN

Attesting Officer

Commissioner of Patents and Trademarks